(12) United States Patent  (10) Patent No.: US 7,795,012 B2
Lehmann et al.  (45) Date of Patent: Sep. 14, 2010

(54) DEVICE FOR PERFORMING ANALYSIS ON CELL CULTURES

(75) Inventors: Mirko Lehmann, Ebnat-Kappel (CH); Martin Brischwein, München (DE); Werner Baumann, Buhl (DE); Ralf Ehret, Merdingen (DE); Ingo Freund, Freiburg (DE)

(73) Assignee: Micronas GmbH, Freiburg (DE)

( * ) Notice: Subject to any disclaimer, the term of this patent is extended or adjusted under 35 U.S.C. 154(b) by 266 days.

(21) Appl. No.: 11/952,219

(22) Filed: Dec. 7, 2007

(65) Prior Publication Data

US 2008/0145922 A1 Jun. 19, 2008

Related U.S. Application Data

(63) Continuation of application No. 10/009,131, filed as application No. PCT/EP00/03860 on Apr. 28, 2000, now abandoned.

(30) Foreign Application Priority Data

May 6, 1999 (DE) ................................ 199 20 811

(51) Int. Cl.
  *C12M 1/34* (2006.01)
(52) U.S. Cl. .................................. 435/288.5; 435/293.1
(58) Field of Classification Search .............. 435/288.5, 435/293.1
  See application file for complete search history.

(56) References Cited

U.S. PATENT DOCUMENTS 4,125,436 A 11/1978 Liner
4,599,315 A 7/1986 Terasaki et al.
4,879,097 A * 11/1989 Whitehead et al. ............ 422/67
5,494,044 A 2/1996 Sundberg
6,193,883 B1 2/2001 Kroner et al.
6,376,233 B1 * 4/2002 Wolf et al. ............... 435/288.4

FOREIGN PATENT DOCUMENTS

| DE | 3242393 | 5/1983 |
|---|---|---|
| DE | 4305405 | 5/1994 |
| DE | 29611336 | 10/1996 |
| DE | 19646505 | 5/1998 |
| DE | 19826153 | 12/1999 |
| EP | 0608153 | 7/1994 |
| EP | 0394406 | 4/1995 |
| EP | 0818540 | 1/1998 |
| FR | 2690926 | 12/1993 |
| WO | 9004645 | 5/1990 |

* cited by examiner

*Primary Examiner*—William H Beisner
(74) *Attorney, Agent, or Firm*—Volpe and Koenig, P.C.

(57) ABSTRACT

A device for investigating activities of cell cultures in a liquid culture medium includes a receptacle for the culture medium, and one or more sensors for measurement of cell culture activities. An opening for adding and removing liquid culture medium is provided. A separating element can be placed close to the receptacle bottom, forming a partial space with a small volume relative to the entire volume. A flow channel that communicates with the small volume and the reservoir and/or the sensors are placed in the small volume partial space. By adjustment of the separating element distance from the receptacle bottom, a microreaction volume exactly fitting the current requirements is obtained. For regeneration of the cell culture solution in the small volume partial space, the separating element can be elevated and depressed, or liquid can be injected into the small volume by the through-flow channel, providing convective mixing of fresh and spent medium.

19 Claims, 3 Drawing Sheets

DEVICE FOR PERFORMING ANALYSIS ON CELL CULTURES

CROSS-REFERENCE TO RELATED APPLICATIONS

This application is a continuation of U.S. application Ser. No. 10/009,131, filed Nov. 13, 2003, now abandoned, that is a 371 National Phase application of PCT/EP00/03860, filed Apr. 28, 2000, which claims the benefit of DE 199 20 811.5, filed May 6, 1999, all of which are incorporated herein by reference as if fully set forth.

BACKGROUND

The invention concerns a device for the carrying out of investigations on living cells, cell cultures and the like, especially for the detection of metabolic activity of the cells, which find themselves in a liquid medium. The device includes at least a receptor for liquid medium along with the cell culture, and wherein one or more measuring apparatuses and/or sensors for measurement of the cell culture are provided and wherein a movable separation element is provided, which confiningly borders a reaction space.

In the case of such a conventional device, fresh culture medium is admitted to the cells in a specified time sequence, or an active agent dissolved in this culture medium is added. Also, exhausted medium is correspondingly removed from the cell culture zone. A substantial regeneration of the culture medium, for example by means of an appropriate fluid system, produces a far-reaching, constant, physiological milieu. Easily dissociating agents, which are added to the nutrient material, likewise can be regenerated. The added medium and the cell culture zone itself must be protected from contamination by microorganisms and from excessive evaporation. These are important preliminary measures for the sensitive measurement of cellular reactions.

Common to all cell culture operations, is a surface on the bottom for the cell storage and cell growth as well as wall surfaces which form a trough for the containment of the culture medium. The culture medium must be regenerated at regular periods, since the waste products of the cell metabolism accumulate. Nutrient substances are consumed and biological active materials decline in their activity in the course of time.

EP 0 394 406 has already disclosed an apparatus for the fluid handling of cell cultures in combination with sensors. The apparatus of this disclosure possesses a tightly sealed, small volume perfusion chamber, in which the cells are cultivated and in which, at the same time, the said chamber is furnished with a sensor. The chamber possesses an inlet and an outlet channel. Driven by a liquid pump, the culture medium flows through the perfusion chamber. In periodic, successive intervals, follow phases with perfusion and phases without perfusion, one after the other. The phases with perfusion serve for regeneration of the culture medium, the phases without perfusion aid the procedure for measurement, that is, the direct follow-up of the extra cellular acidification in the perfusion chamber.

However, it is disadvantageous that a high apparatus expenditure is present, since a liquid drive pump, valves for the control of the liquid flows as well as hose running and all are necessary.

A further disadvantage is that a certain predisposition exists for the formation of air bubbles in the perfusion chamber. These disadvantages can only be excluded at a comparatively high expense. Contributing to the expense, is the fact that equipment for partial degassing of the medium is necessary, which must be coupled with the cell cultures. As a whole, this increases the expense. Finally, a relatively higher labor involvement is required, in order to achieve an air bubble free and an airtight and watertight assembly of the system. This gives a particularly disadvantageous effect, when a multiplicity of parallel samples are to be tested, which is the rule in general practice.

FR-A-2 690 926 discloses a bioreactor, which possesses a container, in which solid particles can be brought into contact with a liquid. In the container is placed a piston, so that the volume of the reactor can be changed.

WO-A-90/04645 makes known a micro-through flow chamber in which cells for investigation as well as a sensor can be found. By means of an inlet and an outlet, the through-flow chamber is in communication with the outside environment.

EP-A-0 608 153 discloses a dosage apparatus with a reaction chamber. Within the reaction chamber a piston is inserted. Laterally, on the wall of the reaction chamber lines are connected, at various distances from the bottom of the reaction chamber, each of which is open or covered, according to the position of the piston.

These three above named documents concern themselves with apparatuses, which are comparatively expensive and complex in construction. An investigation of cells by means of the installation of the different, geometric environmental conditions for cell cultures is, on this account, not possible.

SUMMARY

Thus, the object of the present invention is the creation of a comparatively simple arrangement for the regeneration of the cell culture solutions and the creating of smaller measurement volumes. At the same time, the possibility should be exploited of adapting to geometric environmental conditions which fit the requirements of the cell culture.

To achieve this object, the present invention provides that the separation element be placed in the measurement position, closely above a cell culture on the bottom of the receptacle. Further, the reaction space be separated from the reservoir space wherein the volume of the reservoir space is a magnitude greater than the volume of reaction space. The separating element can have a position either between that bottom proximal location, which covers the cell culture and serves as the measurement position and a bottom distal position, in at least which position, the reservoir stands in fluid communication with the reaction space. The separation element is enabled to take these extreme positions by an essentially vertical up and down motion. Alternately, the separation element can be moved forward and back in a lateral motion between the measurement position and a position in which the reaction space is in fluid communication with the reservoir.

In the position of close juxtaposition with the bottom, the separating element forms a limiting border of a small volume reaction space, which serves for diffusion limitation for substances, which are produced by the cells or consumed by the cells.

With this invented measure, a small volume reaction space is realizable, in which the measurable material changes caused by the cellular metabolism happen much more quickly than in a greater volume. From the speed of change of the pH value, or from the partial pressure of the oxygen in an interval of time, information may be acquired in regard to the activity of the cell metabolism. Advantageous in this matter would be the placement of one or more sensors and/or measurement apparatuses in the confines of this reaction space.

One embodiment of the invention provides, that culture areas which are separated from one another, are formed especially by structured, installed, cell repelling coatings or by a three dimensional profiling of the bottom with recesses or projections in the separative areas therebetween and that in the culture areas the culture medium advantageously exists as respective drops.

With the, for instance, "hand stamp-like" separation element having a flat underside, the drops can be pressed from above and a partial volume is latterly displaced until under the separation element, only a thin liquid film remains to cover the cell culture, which film then forms the reaction space with a microreaction volume of culture medium.

The separation element, in its position proximal to the bottom, partitions off the reaction space from the remaining, drop-like volume of the culture medium which has been outwardly displaced to the side. By means of a lifting motion of the separation element, this said outwardly displaced volume, which serves as a reservoir, mixes with the culture medium remaining in the reaction space and thereby a regeneration of the culture medium remaining in the reaction space is attained.

One embodiment provides, that at least one separation element can take a position in reference to one or more cell culture(s) found on the bottom of a receptacle, and there serve for the lateral displacement of a partial volume of the liquid culture medium which covers the said cell culture and, if required, in that position, is capable of approaching the said cell culture. Cell cultures, for instance, can be placed on a sensor equipped semiconductor wafer in the neighborhood of said sensors. In this case, separation elements can be placed side by side proximal to the cell cultures in such a manner, that one becomes positioned above one of the cell cultures. In this position, measurements can be carried out. It is possible, in this operation, that a plurality of side by side arrayed separation elements can be provided in a somewhat horizontal and, if necessary, vertical distancing from the cell culture.

In this case, the cell culture(s) may be placed on the semiconductor wafer in order to test the sensors after the manufacture of the wafer. Again, the semiconductor wafer with its sensors can form, essentially, the test apparatus with which measurements of cell cultures can be undertaken.

The area of the semiconductor wafer which is exposed cell cultures, can, upon need, can have a confining border to serve as a container for the cell culture medium.

One embodiment of the invention, for which is believed to be independently protectable, provides a container that is open at its top as a receptacle, into which a separation element extends, which subdivides the entire interior space of the said receptacle into two vertically separated volumes, so that the bottom side portion forms a reaction space of small volume in comparison to the entire volume of the receptacle. The other and remaining space forms a reservoir, for which at least one flow channel is provided, which, first, is connected to the reaction space and second is connected to the reservoir space. A further feature is that one or more penetrating, through-flow channels are provided within the separating element, which channels allow communication between the small volume reaction space and the large volume reservoir of the said receptacle.

More advantageous in this case, is the furnishing of one or more sensors or measurement apparatuses in the area of the reaction space.

Also, in this embodiment, by means of the small volume reaction space, it is possible, for instance, to carry through microsensitive measurements where high count cell concentrations are concerned. When this is done, the increased cell count concentration leads to a more rapid change of activity and thereby to an acceleration of the corresponding measurement.

The reservoir, that is set off by the separating element, is found above the reaction space, and in this case can be relatively large in volume, so that the exhausted medium in the reaction space becomes regenerated by a connective mixing with the culture medium from the reservoir, which occurs within a specific time period. This has the advantage that no more culture medium need be added from external sources.

The convective mixing of the culture medium between reaction and reservoir spaces can take place, in that by means of the penetrative, through-flow channels, a definite quantity of culture medium liquid is placed in circulation externally around the reaction space and can also be removed therefrom. The convective mixing is effected by means of the described flow channel.

In accordance with another embodiment of the invention, provision has been made that, the separation element can be moved up and down within the receptacle between a position in proximity to the bottom and a position remote from the bottom.

For the regeneration of the cell culture solution in the reaction space, the possibility exists of lifting the hand-stamp element and then allowing it to settle into its previous position. In this way, a convective mixing of the exhausted medium from the reaction space and the remaining medium in the reservoir space of the receptacle is brought about through the flow channel. The delivery and the removal of a quantity of liquid relating to the microreaction volume is carried out by a mechanical, up and down movement of the separation element.

A complete changeover of the cell culture medium would be dependent on the metabolic activity of the cells and the total volume of the measurement solution, and would only occur at periods of considerable time.

The separation element forms an upper closure of the reaction space, so that a protection from evaporation and contamination is provided. Further, the microreaction volume found therein is buffered by the essentially greater volume of culture medium in the reservoir space, so that any occurring evaporation at the liquid open surface has, in total, very little effect on the microreaction volume.

An advantageous embodiment of the invention provides, that, within the receptacle, the distance of the separating element away from the cell culture, and thereby the proximal position of the same to the bottom is adjustable.

By means of the separating element, which is adjustable as to its distance from the bottom of the receptacle, in the vicinity of the cell culture a microreaction volume can be adjusted to exactly match the current requirements for such a volume. This microreaction volume can, as said, be so adjusted, that only a narrow liquid film of depth from, for example, 50 to 500 µm remains over the cell culture. In this way, the required microreaction volume can be created with correspondingly greater cell concentration.

An advantageous embodiment of the invention provides, that the underside of the separating element possesses a contour which will guide gas bubbles to the outside, preferentially this can be a convex bulge. Air or gas bubbles, with this shaping, can escape and thereby not impair either the cell culture or the sensor measurement thereof. The separating element forms no air tight or liquid tight closure of the cell culture zone, so that the gas bubbles can escape. This arrangement also aids in the assembly of the device, because attention to the freeing of the gas is unnecessary.

It is particularly advantageous, when a plurality of receptacles, forming preferably a part of a pipette automat, are provided. Further, these multiple receptacles can be formed from commercial multiwell plates wherein, in each case, the separating element is provided on the lower end of the pipettes or dispenser channels of the pipette-automats. In this way, these separating elements form a distinct type of a pipette tip.

Directly in connection with a pipetting automat and a multiplicity of, for example, 96 receptacles as cell culture containers, the simple design of the present invention, with the "hand stamp" construction, provides an advantageous effect. Especially, for example, microsensor based measurements can be carried out in such standard cell culture arrays. This practically is not possible with known systems possessing pump instigated through-flow.

In accordance with a development of the present invention, provision has been made for a liquid permeable membrane or a like filter, or a protective covering for the cell culture is provided. In such a case, the membrane, or its equivalent, is placed at a distance from the receptacle bottom, and is located between the cell culture and the separating element which is in its bottom proximal position.

By the integration of such a membrane, which can be designed as a microporous membrane filter, or another protective element to be placed directly over the cell culture, the sensitive cell culture is protected from liquid shear forces and impacts, which can be brought about by the convective mixing and the addition and suction removal of cell culture. Also in this case of integration of the membrane, measurements on non-adherent cell types can be done. Such cell types, otherwise, can be easily rinsed away from the sensors or washed completely out of the small volume reaction space of the receptacle.

In accordance with an embodiment of the invention, the layout surface for the cell culture can be optically transparent. In this way, for instance, the measurements for absorption, dispersion, fluorescence from the cells, can be carried out possibly in accordance with a coloring procedure.

BRIEF DESCRIPTION OF THE DRAWINGS

Additional embodiments of the invention are treated in the further subordinate claims. In the following, the invention is more closely described as to its essential details with the aid of the drawings.

In the drawings, shown somewhat schematically are.

DETAILED DESCRIPTION OF THE PREFERRED EMBODIMENTS

Figure 9:
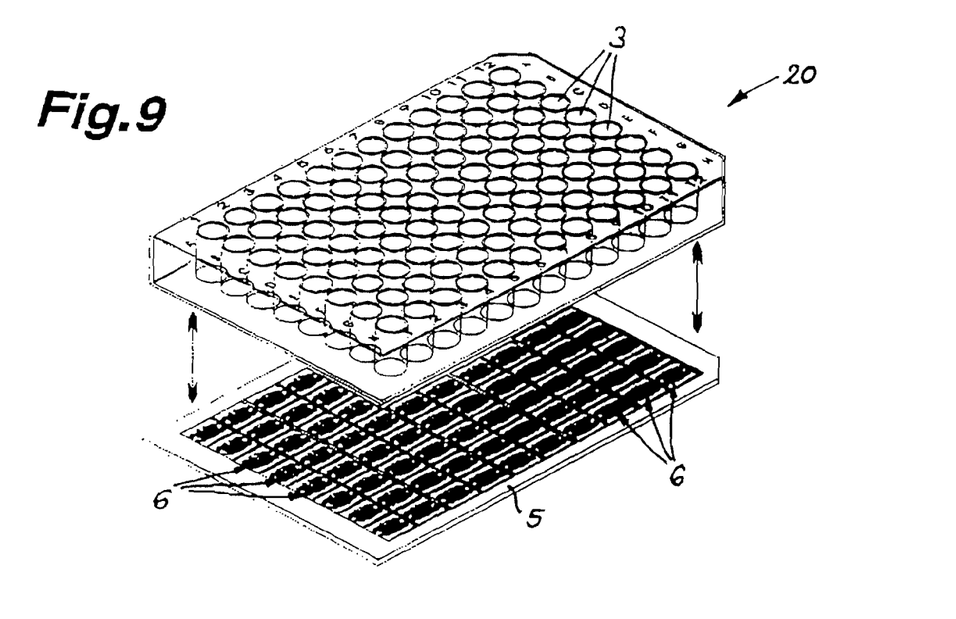
FIG. 9 illustrates a multiplicity of receptacles in the form of a multiwell plate with micro sensor arrays.

A device shown in FIGS. 1 to 7, serves for the investigation of cell cultures 2. The device possesses, for this purpose, preferably a trough like receptacle 3, on the bottom of which, the cell culture is found in a liquid culture medium 4. On this bottom 5 of the receptacle 3, there is found one or more sensors 6, with which measurements of the cell culture 2 can be undertaken. Preferred, as a sensor, is a semiconductor chip particularly provided with a plurality of microsensors 6, whereby even the entire bottom can be designed as a sensor chip, as illustrated in FIG. 9. The sensor-chip combination can execute different sensor functions, for instance, monitoring the activity of ions, oxygen, and the activity of dissolved metabolite. Further, electrical impedance can be tracked as well as temperature and the like.

Figure 1:
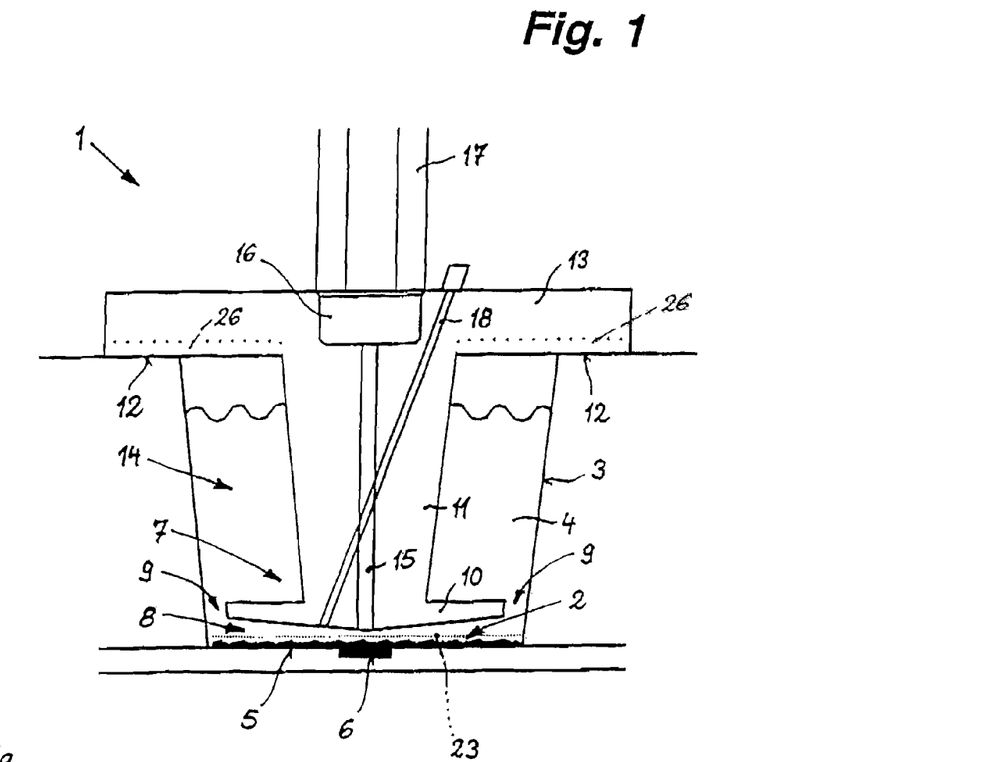
FIG. 1 shows a device for the investigation of cell cultures with a receptacle, a cell culture located therein, as well as a liquid culture medium and a separating element immersed in said culture medium.

The receptacle 3 is open at the top, which allows the insertion of a separating element 7, which, in its bottom proximal position, as can be seen in FIG. 1, provides a limiting boundary for the small volume portion allotted for the reaction space of the receptacle. The separating element 7 has a cross-section somewhat matching the cross-section of the receptacle. Accordingly, between the separating element 7 and the inner wall of the receptacle 3 is an overflow opening 9 serving as a flow channel. In the case of a receptacle diameter of, for example, 5 or 10 mm, this overflow opening 9 shows an open peripheral space of something less than 1 mm in width.

The separating element 7 has, in this embodiment example, a plate shaped head 10 onto which a post like shaft 11 is attached. The side of the separating element 7 proximal to the cell culture, that is, the head 10, is so dimensioned, that it covers- or confines—at least one of the surfaces used for the measurement of such substances which the cells have consumed or produced. This surface can especially be the corresponding surface of a sensor.

Outside of the receptacle 3, the shaft 11 is connected with a cover 13 which overlaps the rim 12 of the receptacle 3. Cover 13 forms in particular a detent for the limitation of the insertion depth of the separating element 7 into the interior of the receptacle 3. The contacting surface of the cover 13 is so constructed, that it does not provide a gas-tight closure. The dotted lines shown, however, indicate corresponding profilings or channels 26. On the rim 12 of the receptacle 3 and/or in the contact area of the cover 13, adjustment means may be provided, by means of which the spatial approach to the receptacle bottom of the separating element 7 within the receptacle 3 is regulated. In accordance with this position of the separating element 7, the size of the reaction space can be varied. Especially, in this manner, adjustment may be to a very small microreaction volume, wherein the proximity of the underside of the head 10 to the cell culture can be, for example, 50 to 500 µm. The portion of space of the receptacle 3 above the head 10 forms a reservoir 14, in which, as in the lower small volume reaction space 8, liquid culture medium 4 is located. The volume of the reservoir can be some 100 times greater than the that of the reaction space 8.

Inside the separating element 7 is provided a penetrating through-flow channel 15, the end of which opens into the reaction space 8. The other end of the through-flow channel 15, in the area of the cover 13, possesses a fitting for connection to a pipette 17 or the like. By means of this through-flow channel, fresh culture medium can be added and exhausted medium removed by suction.

In addition to the through-flow channel 15 opening into the reaction space 8, through flow channels or connection channels can also be provided which open into the reservoir 14. The reference number 18 denotes an electrode or a sensor, which, for example, penetrates the separating element 7 and ends in the partial space 8. For instance, in this place, the electrode 18 may represent the installation of a reference means for a pH or partial pressure of the oxygen.

Figure 8:
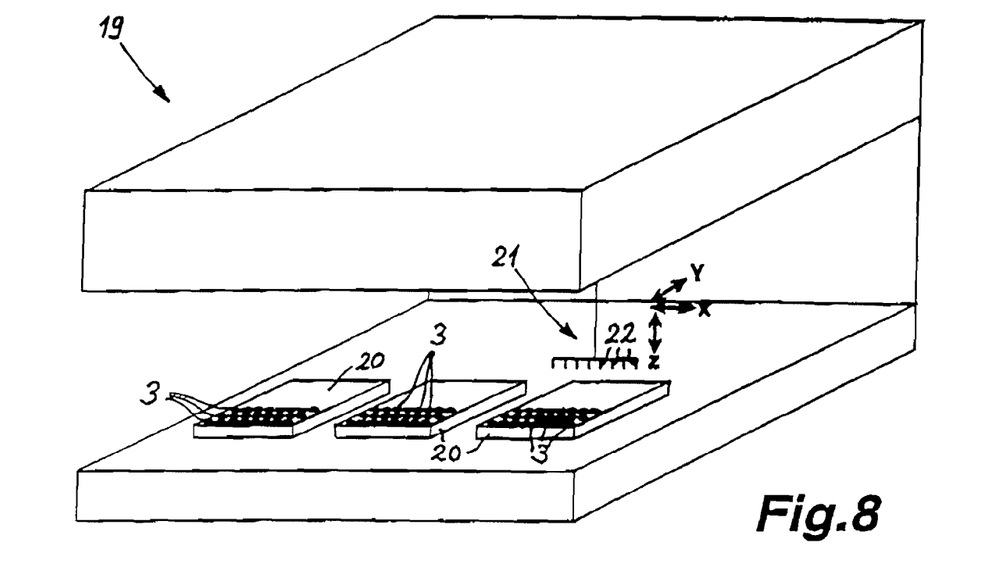
FIG. 8 shows a schematic presentation of a pipetting automat.

The device 1 in accordance with the invention is advantageously installed in connection with a pipette automat 19, which is shown schematically FIG. 8. Clearly shown here are three, multiwell plates 20 with a multiplicity of receptacles 3. Conventionally, such multiwell plates can possess 6, 24 or even 96 receptacles as cell culture containers.

A pipette head 21 with a number of dispenser channels 22 is connected with a (not shown here) positioning apparatus, by means of which the pipette head is movable in a plane in two coordinates and additionally can also be raised vertically. The individual dispenser channels 22 are connected respectively at their free ends with a separating element 7 and can be positioned in such a manner, that the separating element 7, in one or more rows, can be simultaneously inserted into the receptacles 3 in the multiwell plates 20.

With the aid of the pipette automat, at specified time intervals, liquid can be removed from the individual receptacles 3 and transferred to other containers. That is to say, liquid can be removed from certain containers and fed to those receptacles provided with cell cultures. Principally, in this way, a periodic regeneration of the microreaction volume in the small volume partial space 8 can be effected as well as in the vicinity of the sensors 6, and further, also in the living cell culture. The microreaction volume in this activity is not comprised of a closed perfusion chamber and the regeneration is not by means of allowing a through-flow of a solution, as was known in the state of the art, but is achieved on the other hand by the design of the separating element 7 in connection with the steps of the following procedure.

Figure 2:
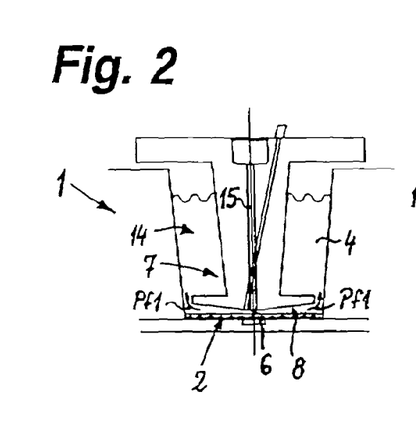
FIG. 2 to 4 show the device of FIG. 1 in various operational situations.
Figure 3:
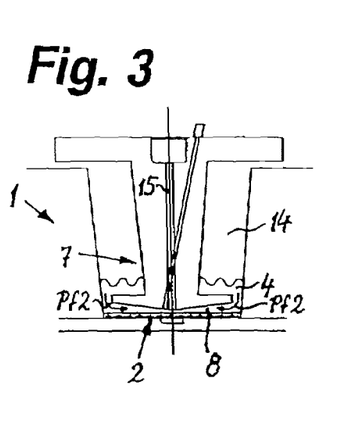
Figure 4:
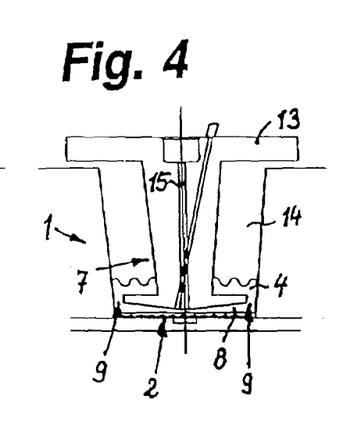

For this purpose, in the FIGS. 2 to 4, an operational mode is demonstrated, in which an intermix of the liquid cell culture medium is carried out by means of periodic supply and withdrawal of the cell culture medium.

Figure 5:
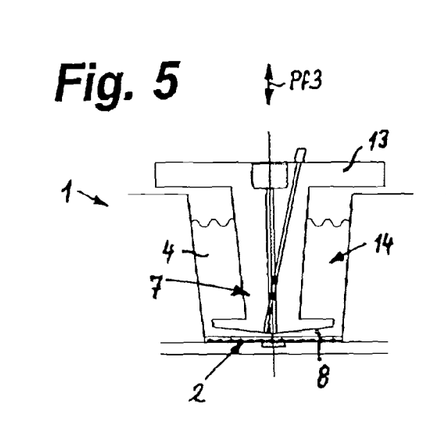
FIG. 5 to 7 show the device of FIG. 1 with the separating element in various positions.
Figure 6:
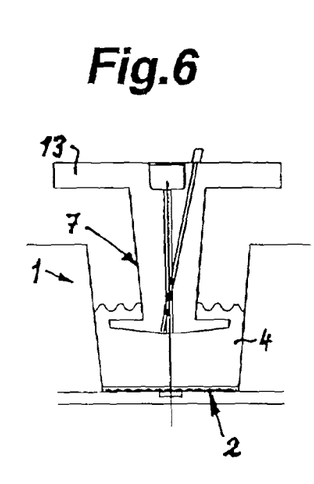
Figure 7:
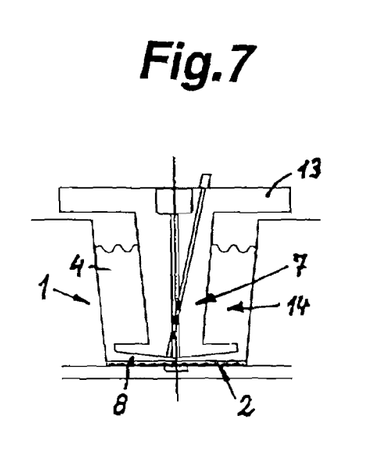

The other operational mode is clearly shown in FIGS. 5 to 7. In this case the intermix of the cell culture medium is effected by a periodic lifting and lowering of the separating element 7.

In the FIGS. 2 to 7, for the sake of simplicity, the dispenser channel 22 normally bound to the connection piece (FIG. 1) 16 is omitted. By means of this, the feed and suction removal of culture medium is carried out. A pipette 17, or a dispenser channel 22 is easily seen in FIG. 1 or FIG. 8.

In the operational mode in accordance with FIGS. 2-4, the separating element 7, found at the lower end of a dispenser channel 22 of a pipette head 21, is inserted into a receptacle 3 and thereby, the cell culture is provided with nutrient to the extent, that the head 10 of the separating element 7 defines the upper side of a small volume reaction space 8, whereby the liquid volume can, for instance, run to a few microliters. In this position of the separating element 7, i.e. with its head 10 close to the bottom, for instance, a microsensor measurement of the metabolism of the cell culture 2 can be carried out. At the same time, from the rate of change of the pH or from the partial pressure of the oxygen during this test interval, information can be derived in regard to the activity of the metabolism.

In a subsequent time interval, then, there is carried out a regeneration of the culture medium in the microvolume inside the reaction space 8. By means of the through-flow channel 15, for this purpose, a specified fluid quantity of culture medium is added to the reaction space 8, whereby culture medium from the reaction space 8, in accord with the arrow Pf1, is expelled into the reservoir 14, where a convective intermix of fresh and exhausted media takes place. Subsequently, an equal fluid quantity is removed by suction through the channel 15, so that, from the reservoir 14, according to the arrow Pf2, culture medium flows out of the reservoir 14 into the reaction space 8. Following this, then, in an idle interval, (FIG. 4), where no through-flow takes place, for example, the next micro-measurement is made. In this described operational mode, based on the FIGS. 2 to 4, essentially only the microreaction volume is periodically exchanged, not, however, the volume in the reservoir of the receptacle 3. Through the addition and the removal by suction of the fluid quantity, practically a "pump action" is achieved resulting in the intermixing of the liquid cell culture medium in the reaction space 8 and the culture medium in the reservoir 14.

In specified intervals of time, a fluid quantity is removed and this is transferred to a waste container and subsequently fresh medium from a supply vessel is removed by suction and filled into the receptacle 3 which is supplied with a cell culture.

The mode of operation in accordance with FIGS. 5 to 7, provides that the separating element 7, be operated in a vertical movement, which is executed at prescribed intervals of time and directionally in accord with the double arrow Pf3. Should the separating element 7 find itself in the lower position (FIGS. 5 to 7), then the provided microreaction volume with in the reaction space 8 is available for a measurement. After the measuring interval, the separating element 7 is raised and by means of this motion upward, a convective intermix of the exhausted culture medium originally found in the reactions space 8 with the remaining culture medium of the reservoir 14, and in this way, a homogenizing of the cell culture medium takes place. This process repeats itself periodically. A complete exchange of the cell culture medium would be only due in an "nth" period of time, dependent upon the activity of metabolism of the cells and the volume of the measurement solution. The regeneration of the culture medium found in the reaction space 8 would be done in this case by a mechanical movement of the "hand stamp" shaped separating element 7 and by means of mixing with unused culture medium from the reservoir 14.

In both operational modes, because of the large reservoir 14, there stands available a relatively large volume of cell culture medium as compared to that in the reaction space 8, which, by means of convectional mixing with the cell culture medium out of the microreaction volume, makes possible a relatively long dwell time, until finally an exchange of the culture medium must be made.

By means of the arrangement in accordance with the present invention, which dispenses with an allowable continuing or successive through-flow of cell culture solutions, the problems therewith associated are avoided. The arrangement can be so designed with simple means, that it is compatible to widely used cell culture formats such as is, for example, the 96-well, multi-tier plate, as well as to an installation in cell culture incubators. The inventive procedures can logically, as already described, be combined with a pipette automat, in order to achieve a non-manual regeneration of the cell culture solutions.

In the FIGS. 1 to 7, one can plainly observe, that the underside of the head 10 of the separating element 7 is convex and bowed downward, in order to bring about a situation in which the gas bubbles move to the perimeter thereof and by means of the overflow opening 9, eventually escape to the ambient surroundings. Since the cover 13 does not provide a tight closure of the receptacle 3, which is indicated by the dotted lines 26 in FIG. 1, a gas exchange between the culture medium and the ambient atmosphere is assured. In spite of this non-tight closure of the receptacle 3, a sufficient protection from evaporation of the cell culture solution is assured and the infiltration of microbiological contamination is prevented. The channels 26 are in their cross section, correspondingly small dimensioned. The entire separating element 7 with the cover 13 is comprised advantageously of a smooth, cell-rejecting, inert and easily sterilized material.

Further, as is noticeable in the FIGS. 1 to 7, is that, at a distance from the bottom 5 of the receptacle 3, and between this and the separating element 7 which is in its bottom proximal position, a microporous membrane 23 is provided as a protective cover for the cell culture. By means of this microporous membrane filter, the sensitive cell culture is protected from liquid shear forces, and impacts, all of which can come about through the convective mixing of and the addition and suction removal of cell culture media. Especially in the case of non-adherent cell types, protection is given so that these will not be washed away by the flows of liquids.

FIG. 9 shows a multiwell plate 20 before the closure of an upper part and a lower part. In the embodiment shown here, for the receptacles 3 of a conventional microtiter plate, the bottom area is separated, so that small through-flow tubes can be accommodated. The microtiter plate upper part is then set upon a substrate plate 24, and preferably, made tight with this by ultrasonic welding. The substrate plate 24 with the respective sensors forms then the bottom of the receptacles 3. The sensors, or sensor arrays, when a microtiter plate is employed, are placed in the intervening distances between the individual small tubes or individual receptacles.

In keeping with the practice of previously installed apparatuses in connection with conventional microtiter plates, by the use of the upper part of a microtiter plate to form the receptacle 3, the possibility arises of being able to install, without change as shown in the pipetting automat seen in FIG. 8, a sampling automat, a microplate reader, and the like.

The sensors 6 can be formed by sensor arrays with several, different individual sensors. On the substrate plate can be found a control and evaluation apparatus, or parts thereof.

Besides electronic sensors on a semiconductor base, also other sensors can be provided on, for instance, optical, thick film technology, or biological bases and advantageously installed in combination with the previously described sensors.

Further there is the possibility, that on the underside of the semiconductor-substrate plate 24, a heating layer can be applied, by means of which a temperature control of the substrate plate can be activated. Then, as far as temperature is concerned, the normal life conditions for cell cultures can be created, so that researches over a longer time period are possible. There is also the possibility, that instead of a continuous heating layer, partial, sections of heating layers which are separate from each other can be provided, in order, on a needed basis, to be able to produce different temperatures in specific areas. For the thermostatic control of the heating, at one or more locations of the substrate plate, temperature measuring sensors can be provided. Such temperature measurement sensors can also be integrated directly in the individual sensors 6 of the receptacles. Temperature measuring sensors in the area of the individual receptacles can be used, besides for the thermostatic control of heating, for the determination of the biological activity of the cells.

Figure 10:
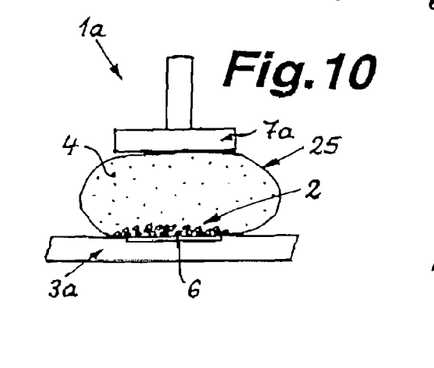
FIGS. 10 and 11 show a culture medium drop on an receptacle bottom with a separating element in different positions.
Figure 11:
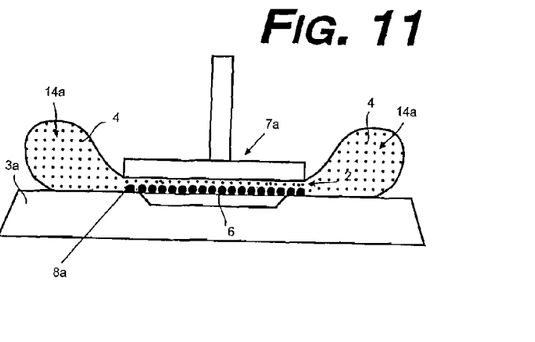

FIGS. 10 and 11 show an embodiment of the device 1a in accordance with the invention, in which a plate shaped receptacle 3a is provided, the upper side of which carries the sensors 6. In the area of this or of the sensors 6, the liquid culture medium 4 is applied as drops. This drop of culture medium covers over the cells which are to be found on the sensors 6, that is to say, a cell culture 2.

To create a small volume reaction space 8a, the separating element 7a, which is shown in FIG. 10 as placed the upper side of the drop 15, is brought into a position proximal to the bottom, as this is depicted in FIG. 11. Upon moving the "hand stamp" shaped separating element 7a downward, the drop 25 is deformed and a portion of its volume is forced laterally outward. Underneath the separating element 7a, as a projection of its elongation, there then remains between the cell culture 2 and the essentially flat underside of the separating element 7a, a thin liquid film with a correspondingly small volume, which can be essentially smaller than the said laterally displaced volume of the drop 25.

Thus, there now exists, first, as described with the aid of the embodiment of the invention shown in FIGS. 1 to 7, a small volume reaction space 8a and second, a reservoir 14a is made available by means of the culture medium laterally displaced by the projection of the separating element 7a. If the culture medium 4 in the gap shaped reaction space 8a is exhausted by the reaction of the cells, then the separating element 7a can be slightly raised, whereupon culture medium, from the laterally displaced drop zone, migrates underneath the separating element 7a and intermixes with the exhausted culture medium located there. Subsequently, the separating element 7a is again depressed, so that once again a small volume reaction space 8a is formed, whereby now, in this space, a regenerated culture medium is located. Subsequently, then again, a measurement phase is instituted. This arrangement can advantageously be put to use, in order to carry out functional tests of the sensors on unsawn chip wafers.

The plate shaped receptacle 3a can be designed somewhat in the manner of the substrate plate 24 of FIG. 9, whereby the individual sensor areas can be separated, one from the other by means of installed, structured, cell repellant coatings. In this case, the bottom of the receptacle forms a part one of the wafers which possess sensors.

Mention should also be made, that the plate shaped receptacle 3a (FIGS. 10, 11), that is, the equivalent of the bottom 5 of the receptacle 3 (see FIGS. 1 to 7) can be optically transparent, so that the cell culture or the culture medium found in this zone is accessible, preferably from below, for optical measurement apparatuses.

What is claimed is:

1. A device for carrying out of investigations on living cells, cell cultures and for detection of metabolic activity of the cells, which are located in a liquid medium, the device comprises at least one receptacle for liquid medium along with the cell culture, and wherein one or more measuring apparatuses and/or sensors for measurement of the cell culture are provided and wherein a movable separating element is provided, which confiningly borders a reaction space, the separating element (7, 7a) is placed in a measurement position, closely above a cell culture on a bottom of the receptacle to separate a reaction space (8, 8a) from a reservoir space wherein a volume of the reservoir space is an order of magnitude greater than a volume of the reaction space (8, 8a), and the separating element (7, 7a) is movable through one of an essentially vertical up and down motion, from a bottom proximal location, which covers the cell culture and serves as the measurement position, and a bottom distal position, in at least which position, the reservoir (14, 14a) is in fluid communication with the reaction space (8, 8a), or a forward and back, lateral motion between the measurement position and a position in which the reaction space (8, 8a) is in fluid communication with the reservoir (14, 14a), the one or more measuring apparatuses and/or sensors comprises at least one sensor that is placed on, or in, the bottom of the receptacle (3a) and culture areas separated from one another, are formed by application of structured, cell repellent coatings or created by a three dimensional contouring of the bottom with recesses or elevations defining separated areas therebetween, and the culture medium (4) in the culture areas is respectively present as drops (25), the bottom of the receptacle is formed by at least one part of at least one wafer upon which the at least one sensor (6) is provided, and an open top container, is provided as a receptacle (3), into which the separating element (7) extends, which divides the space of the entire receptacle (3) into two space portions, one positioned above the other, and a bottom side space portion forms a small volume reaction space (8) in comparison to an entire volume of the receptacle (3) and the other space portion forms a reservoir (14) and at least one flow channel (9) is provided, which first, communicates with the reaction space (8) and second, communicates with the reservoir space (14) and within the separating element (7) one or more through-flow channels (15) are provided, which open into the small volume reaction space (8) of the receptacle (3) and/or in the reservoir space (14) of the receptacle (3).

2. A device in accordance with claim 1, wherein the movable separating element comprises at least one separating element for one or more cell culture(s) (2) located on the bottom of the receptacle that can be positioned into such close proximity to said cell culture, as to respectively laterally displace a partial volume of the liquid culture medium (4) which covers the cell culture.

3. A device in accordance with claim 1, wherein the one or more measuring apparatuses and/or sensors are placed in the area of the reaction space (8, 8a).

4. A device in accordance with claim 1, wherein the separating element (7) within the receptacle (3) is movable, back and forth, between a position proximal to the bottom and a position remote from the bottom and in the position proximal to the bottom borders the reaction space (8).

5. A device in accordance with claim 1, wherein a side of the separating element (7) proximal to the bottom, possesses a cover, that is, a bordering surface, for measurement of substances consumed or produced by the cells on a surface corresponding to a sensor surface of the one or more measuring apparatuses and/or sensors.

6. A device in accordance with claim 1, wherein the separating element (7) can be inserted from above into the receptacle (3).

7. A device in accordance with claim 1, wherein a distance of the separating element (7) from the cell culture (2) and therewith the bottom proximal position of the said separating element (7) is adjustable.

8. A device in accordance with claim 1, wherein the separating element (7) is constructed with a hand stamp shape and has a head (10) with approximately an equal cross-section to that of the receptacle (3), and which separating element (7) divides the receptacle into a reaction space (8) and a reservoir (14) and on the separating element (7) a shaft (11) is connected which extends to outside, an outside cross-section of the shaft (11) is smaller than an open inside cross-section of the receptacle (3) and an intervening space between the shaft and an inner wall of the receptacle (3) forms the reservoir (14).

9. A device in accordance with claim 1, wherein within the separating element (7) one or more flow channels are provided which first, open in the reaction space (8) and second open in the reservoir space (14).

10. A device in accordance with claim 1, wherein the flow channel (9) is formed by an annular gap provided between the separating element (7) and an inner wall of the receptacle (3) or comprises a rim profiling, and the flow channel remains available, in the case of a separating element (7) which can be adjusted as to height, at least within a lift interval between a position proximal to the bottom and a position remote therefrom.

11. A device in accordance with claim 1, wherein a thrust limitation for the separating element (7) is provided and in the bottom proximal position an effective restraint is placed on the separating element (7) by a detent abutted by an upper rim (12) of the receptacle (3).

12. A device in accordance with claim 11, wherein the detent placed on the upper receptacle rim (12) by the separating element (7) comprises a cover (13) which overlaps the rim (12) of the receptacle (3) or alternately includes a conical section which engages in a counter conical section of the receptacle opening.

13. A device in accordance with claim 1, wherein a receiving volume of the reservoir (14, 14a) is a multiply greater than the volume of the reaction space (8, 8a) and the two volumes are in relation to one another by ratios of respectively, 10:1 to approximately 100:1.

14. A device in accordance with claim 1, wherein at a distance from the receptacle bottom and between the bottom and the separating element (7) in a bottom proximal position, a microporous membrane (23) or filter or protective covering for the cell culture is provided.

15. A device in accordance with claim 1, wherein the separating element (7) is comprised of a smooth, cell rejecting, inert and easily sterilized material.

16. A device in accordance with claim 1, wherein a resting surface for the cell culture (2) is optically transparent and the resting surface is related to an optical measuring apparatus, which is situated on the underside.

17. A device in accordance with claim 1, wherein the receptacle comprises a plurality of receptacles (3) as a part of a pipetting automat (19) and the receptacles (3) comprise commercially available multiwell plates (20) and on lower ends of dispenser channels of the pipetting automat, respectively, the separating element (7) is provided.

18. A device for carrying out of investigations on living cells, cell cultures and for detection of metabolic activity of the cells, which are located in a liquid medium, the device comprises at least one receptacle for liquid medium along with the cell culture, and wherein one or more measuring apparatuses and/or sensors for measurement of the cell culture are provided and wherein a movable separating element is provided, which confiningly borders a reaction space, the separating element (7, 7a) is placed in a measurement position, closely above a cell culture on a bottom of the receptacle to separate a reaction space (8, 8a) from a reservoir space wherein a volume of the reservoir space is an order of magnitude greater than a volume of the reaction space (8, 8a), and the separating element (7, 7a) is movable through one of an essentially vertical up and down motion, from a bottom proximal location, which covers the cell culture and serves as the measurement position, and a bottom distal position, in at least which position, the reservoir (14, 14a) is in fluid communication with the reaction space (8, 8a), or a forward and back, lateral motion between the measurement position and a position in which the reaction space (8, 8a) is in fluid communication with the reservoir (14, 14a), and the separating element (7) possesses on an upper side thereof, an opening for coupling with a pipette, a pipette tip, or a dispenser channel.

19. A device for carrying out of investigations on living cells, cell cultures and for detection of metabolic activity of the cells, which are located in a liquid medium, the device comprises at least one receptacle for liquid medium along with the cell culture, and wherein one or more measuring apparatuses and/or sensors for measurement of the cell culture are provided and wherein a movable separating element is provided, which confiningly borders a reaction space, the separating element (7, 7a) is placed in a measurement position, closely above a cell culture on a bottom of the receptacle to separate a reaction space (8, 8a) from a reservoir space wherein a volume of the reservoir space is an order of magnitude greater than a volume of the reaction space (8, 8a), and the separating element (7, 7a) is movable through one of an essentially vertical up and down motion, from a bottom proximal location, which covers the cell culture and serves as the measurement position, and a bottom distal position, in at least which position, the reservoir (14, 14a) is in fluid communication with the reaction space (8, 8a), or a forward and back, lateral motion between the measurement position and a position in which the reaction space (8, 8a) is in fluid communication with the reservoir (14, 14a), and the separating element (7) on its end distal to the bottom, includes a fitting for connection to, or plugging into, a dispenser channel (22) of a pipetting automat.

* * * * *